US009284446B2

(12) United States Patent
Vince et al.

(10) Patent No.: US 9,284,446 B2
(45) Date of Patent: Mar. 15, 2016

(54) SOLUBLE AQUEOUS COMPOSITIONS OF ZINC SALTS OF SELECTED POLYITACONIC ACID POLYMERS

(71) Applicant: Itaconix Corporation, Stratham, NH (US)

(72) Inventors: Martin Vince, Etobicoke (CA); Anita Augustyniak, Portsmouth, NH (US); Yvon Durant, Lee, NH (US); John Shaw, Hampton Falls, NH (US)

(73) Assignee: Itaconix Corporation, Stratham, NH (US)

( * ) Notice: Subject to any disclaimer, the term of this patent is extended or adjusted under 35 U.S.C. 154(b) by 0 days.

(21) Appl. No.: 14/582,637

(22) Filed: Dec. 24, 2014

(65) Prior Publication Data

US 2015/0183978 A1  Jul. 2, 2015

Related U.S. Application Data

(60) Provisional application No. 61/920,894, filed on Dec. 26, 2013.

(51) Int. Cl.

| C08L 35/00 | (2006.01) |
|---|---|
| C12P 7/44 | (2006.01) |
| C08F 122/02 | (2006.01) |
| C08F 122/04 | (2006.01) |
| C08F 2/38 | (2006.01) |

(52) U.S. Cl.
CPC . *C08L 35/00* (2013.01); *C08F 2/38* (2013.01); *C08F 122/02* (2013.01); *C08F 122/04* (2013.01); *C12P 7/44* (2013.01); *C08L 2201/54* (2013.01)

(58) Field of Classification Search
CPC .................. C08L 35/00; C08K 2003/2296
USPC ................................. 524/559, 432
See application file for complete search history.

(56) References Cited

U.S. PATENT DOCUMENTS

| 4,138,477 A | 2/1979 | Gaffar |
| 4,425,321 A | 1/1984 | Jacquet et al. |
| 5,223,592 A | 6/1993 | Hughes et al. |
| 5,336,744 A | 8/1994 | Swift et al. |
| 6,632,421 B2 | 10/2003 | Ascione et al. |
| 7,910,676 B2 | 3/2011 | Durant et al. |
| 7,910,677 B2 | 3/2011 | Durant et al. |
| 7,915,365 B2 | 3/2011 | Durant et al. |
| 8,227,560 B2 | 7/2012 | Durant et al. |

OTHER PUBLICATIONS

"Polymerization of Itaconic Acid in Aqueous Solution: Structure of the Polymer and Polymerization Kinetics at 25° C. Studied by Carbon-13 NMR", Grespos et al, Makromolekulare Chemie, Rapid Communications (1984), 5(9), 489-494.

*Primary Examiner* — Vu A Nguyen
(74) *Attorney, Agent, or Firm* — Grossman, Tucker, Perreault & Pfleger, PLLC

(57) ABSTRACT

The present invention relates to soluble aqueous compositions comprising metal salts of selected polyitaconic acid (PIA) resins.

17 Claims, 6 Drawing Sheets

SOLUBLE AQUEOUS COMPOSITIONS OF ZINC SALTS OF SELECTED POLYITACONIC ACID POLYMERS

CROSS-REFERENCE TO RELATED APPLICATIONS

This application claims the benefit of U.S. Provisional Patent Application Ser. No. 61/920,894, filed on Dec. 26, 2013, which is fully incorporated herein by reference.

FIELD OF THE INVENTION

The present invention relates to soluble aqueous compositions comprising metal salts of selected polyitaconic acid (PIA) resins. More specifically, the invention relates to soluble solutions of zinc salts of polyitaconic acid where the polymer MW, polymer tacticity, weight ratio of zinc to polymer, concentration of zinc and polymer in the aqueous composition and pH are all adjusted to provide improved performance for various identified consumer applications.

BACKGROUND

The polymerization of vinyl type monomers that contain pendant carboxylic acid functionality has always presented some unique challenges. For example, U.S. Pat. No. 5,223,592 reports that the critical aspect is to provide complete neutralization of an itaconic acid type monomer prior to conducting the polymerization reaction, where complete neutralization is identified as having two moles of base neutralizer for each mole of itaconic acid. U.S. Pat. No. 5,336,744 reports that polymers of itaconic acid are formed at high conversion by an aqueous polymerization process of partially neutralized monomer solution, water, polyvalent metal ion, and initiator. U.S. Pat. No. 7,910,676 relates to methods and polymers based upon vinyl type monomers that contain pendant carboxylic acid groups and ester group functionality. U.S. Pat. No. 7,910,677 stands directed at detergents formed from such polymers, and U.S. Pat. No. 7,915,365 stands directed at absorbent materials also formed from such polymers. U.S. Pat. No. 8,227,560 stands directed at polymers that again have pendant carboxylic acid groups and/or ester functionality and wherein the polymer indicates $^{13}$C NMR triads having a syndiotacity of greater than 58%.

U.S. Pat. No. 4,238,477 recites compositions to prevent and control mouth odor that employs a combination of a zinc compound and an anionic polymer. U.S. Pat. No. 4,425,321 recites deodorant compositions comprising zinc and polyacids of various indicated structures.

SUMMARY

A soluble aqueous composition of a zinc salt of a polyacid comprising the following repeating units:

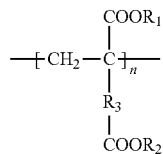

wherein $R_1$ and $R_2$ are selected from a hydrogen atom or an alkyl group or an aromatic group, or a cyclic alkyl group or a polyether, and combinations thereof and $R_3$ may be selected from an alkyl group, aromatic functionality, hetero aromatic functionality, cyclic alkyl group, heterocylic group, or combinations thereof, wherein at least 50 mole % of $R_1$ and $R_2$ are a hydrogen atom to provide carboxylic acid functionality for zinc salt formation and the polyacid is characterized as having:

(1) $^{13}$C NMR triads having a syndiotacticity of greater than 58.0%; and (2) the value of n for the indicated repeating unit provides a number average molecular weight (Mn) of 500-5000;

wherein the weight ratio of Zn to the polyacid is in the range of 0.01-0.15 and the concentration of the polyacid in the aqueous composition is 5-15% by weight and the concentration of Zn in the aqueous solution is 0.5-2.0% by weight and the pH of said aqueous composition is in the range of 3.0-11.0.

BRIEF DESCRIPTION OF THE DRAWINGS

The above-mentioned and other features of this disclosure, and the manner of attaining them, will become more apparent and better understood by reference to the following description of embodiments described herein taken in conjunction with the accompanying drawings, wherein.

DETAILED DESCRIPTION

Figure 1:
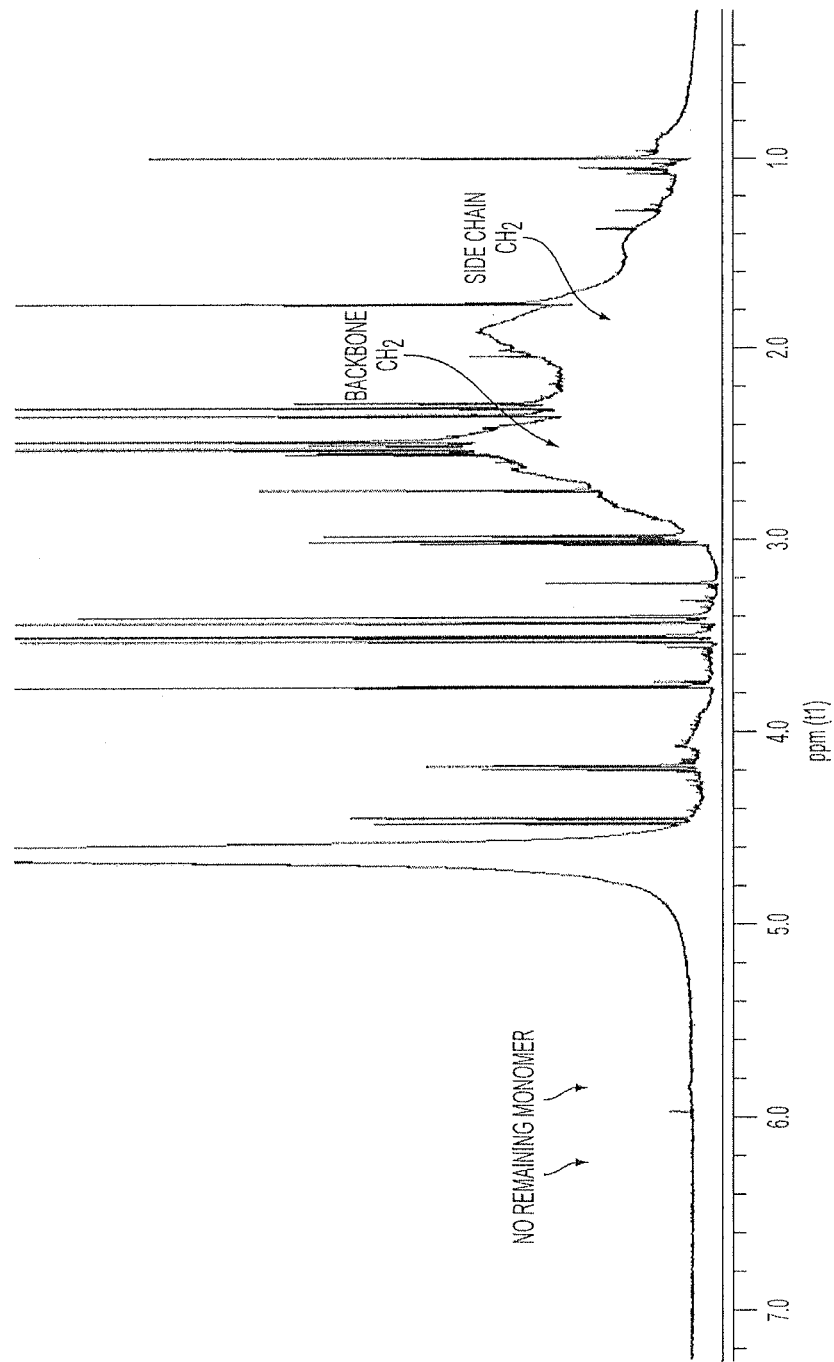
FIG. 1 shows the 400 MHz $^1$H NMR spectra of poly(itaconic acid) in $D_2O$ corresponding to Synthesis A.

Throughout the description, like reference numerals and letters indicate corresponding structure throughout the several views. Also, any particular feature(s) of a particular exemplary embodiment may be equally applied to any other exemplary embodiment(s) of this specification as suitable. In other words, features between the various exemplary embodiments described herein are interchangeable as suitable, and not exclusive.

It may be appreciated that the present disclosure is not limited in its application to the details of construction and the arrangement of components set forth in the following description or illustrated in the drawings. The embodiments herein may be capable of other embodiments and of being practiced or of being carried out in various ways. Also, it may be appreciated that the phraseology and terminology used herein is for the purpose of description and should not be regarded as limiting. The use of "including," "comprising," or "having" and variations thereof herein is meant to encompass the items listed thereafter and equivalents thereof as well as additional items.

The monomers suitable for polymerization herein include vinyl type monomers that have the following general structure:

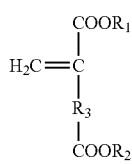

wherein $R_1$ and $R_2$ are selected from a hydrogen atom or an alkyl group (e.g. —$(C_nH_{2n+1})$ where n has a value of 1-18), or an aromatic group, or a cyclic alkyl group or a polyether, and combinations thereof. In addition, $R_3$ may be selected from an alkyl group, aromatic functionality, heteroaromatic functionality, cyclic alkyl group, heterocylic group, or combinations thereof, wherein at least 50 mole % of $R_1$ and $R_2$ are a hydrogen atom to provide carboxylic acid functionality. In addition, in a particularly preferred embodiment, R1 and R2 are both hydrogen atoms, which therefore provides the monomer generally known as itaconic acid.

An alkyl group may be understood to include combinations of carbon and hydrogen, including unsaturated carbon-carbon linkages, which are not prone to polymerization, such as radical polymerization. Furthermore, the number of carbon atoms in the alkyl group as alluded to above may be in the range of 1-18, including all values therein in 1 carbon increments. In addition, reference to heteroaromatic functionality may be understood as reference to an aromatic ring containing a heteroatom (e.g., nitrogen, oxygen, sulfur or phosphorous) and reference to a heterocyclic group may be understood as reference to a non-aromatic carbon ring structure also containing one or more heteroatoms.

In addition, it should be noted that the vinyl type monomers with the above indicated structure, when in acidic form, may be optionally partially or completely neutralized with any base such as monovalent inorganic bases, e.g, $M^+[OH-]_x$ where M represents a cationic moiety selected from sodium, potassium, and/or lithium and x assumes a value to provide a neutralized salt. In addition, it is contemplated herein that one may employ non-metallic hydroxides, such as ammonium hydroxide, as well as organic base compounds, including primary and other amines (e.g., an alkyl amine such as monomethyl amines, dimethyl amines, trimethylamines, monoethylamine, diethylamine, triethylamine).

Comonomers may also be employed in conjunction with the above monomeric compounds, which may then provide random copolymer structure. With respect to the use of any comonomer, it should be appreciated that the vinyl monomers noted above containing the indicated $R_1$, $R_2$ and $R_3$ functionality may be preferentially present at a level of equal to or greater than 50 wt. %.

The comonomers that may then be utilized include any vinyl type monomer that would be suitable for copolymerization, including, but not limited to acrylate monomers (such as methyl methacrylate, methyl acrylate, 2-hydroxyethyl acrylate, polyethyleneoxidediacrylate), vinyl acetate, vinyl halides, styrene, acrylamides, olefin monomers (e.g. ethylene or propylene) and acrylonitrile. In addition, the comonomers may include vinyl type anhydride monomers, such as maleic acid anhydride, itaconic acid anhydride as well as other acidic functionalized monomers, such as citraconic acid or measaconic acid (however, as noted herein, the levels of these latter monomers may require selected control of the concentration in the polymerization medium). Comonomers may also extend to water soluble type monomers, such as vinyl alcohol or vinyl acetate-vinyl alcohol mixtures.

Neutralization

It has been found that to provide for relatively more efficient polymerization and in particular relatively high conversion (e.g. conversion of at or greater than 75% wt of the monomer) the monomers identified herein may preferably be first neutralized under selected conditions in order to optimize the ensuing polymerization which may then improve values of conversion and/or molecular weight. The molecular weights that are improved may include the number average molecular weight (Mn) and/or weight average molecular weight (Mw).

Neutralization may be accomplished by treatment of the acidic monomers with any base, such as monovalent inorganic bases, e.g., $M^+[OH^-]_x$ wherein M represents a cationic moiety selected from sodium, potassium, lithium and x assumes the value to provide a neutralized salt. In addition, it is contemplated herein that one may employ non-metallic hydroxides, such as ammonium hydroxide, as well as organic base compounds, including primary amines (e.g. an alkyl amine such as monomethyl amines, dimethylamines, trimethylamines, monoethylamine, diethylamine, triethylamine) and/or organic compounds containing hydroxyl (OH) group functionality (e.g. ethylene glycol).

The amount of neutralization may be adjusted to provide a less than complete neutralization of the acidic groups present on the vinyl monomers noted herein. For example, in the case of the representative monomer of itaconic acid, it may be understood that complete neutralization will require two moles of neutralizer for each mole of itaconic acid. That is, two moles of sodium hydroxide would provide complete neutralization of one mole of itaconic acid, and any amount of sodium hydroxide less than two moles would provide the desired result of partial neutralization.

Those of skill in the art would recognize that when a divalent based is employed to neutralize itaconic acid, the amount of divalent base selected to completely neutralize itaconic acid would be 1.0 mole of divalent base for each mole of itaconic acid, and to partially neutralize, less than one mole of divalent base may be applied to partially neutralize the itaconic acid monomer.

It has been found that the level of neutralization herein may be preferentially maintained at about 25.0 mole % to 85.0 mole %, including all values therein, in 1.0 mole % increments. For example, for a 1.0 moles of itaconic acid, one may preferably neutralize 0.25 moles of the acid groups present to 0.85 moles of the acid groups present. More preferably, the level of neutralization may be maintained at a level of 40.0 mole % to 60.0 mole %, and in a most preferred embodiment, the level of neutralization of the acid monomer selected may be in the range of 45.0 mole % to 55.0 mole %.

The temperature at which partial neutralization may be achieved may also be adjusted such that neutralization is accomplished at temperatures of 50.0° C. to 150° C., including all values therein, in 1.0° C. increments. For example, it is preferable that the neutralization temperature is adjusted to be 50° C. to 110° C., and in a most preferred configuration, the neutralization temperature is adjusted to be in the range of 65° C. to 100° C.

The time for neutralization has also emerged as another variable to regulate and may also be selected herein to occur for a selected and relatively limited period of time prior to any ensuing polymerization. For example, one may partially neutralize according to the requirements noted above and allow for such partial neutralization to remain at the previously specified neutralization temperatures for a period of time up to and including 6.0 hours, including all time periods between 0.1 hours to 6.0 hours, in 0.1 hourly increments. More preferably, the neutralization time period at the previously specified temperature may be selected such that it does not exceed a time period of 2.0 hours. Finally, the neutralization time period at the previously specified temperature may be preferably selected such that it does not exceed a time period of 1.0 hours.

In addition, it may be appreciated that one may accomplish neutralization by, e.g., operating for no more than an accumulated time period of 6.0 hours at a temperature of 50° C. to 150° C., by cooling outside such temperature and time period, to otherwise limit isomerization of the reacting monomers, as discussed more fully below. For example, one may partially neutralize as noted above for a period of 0.5 hours at a temperature of 50° C. to 150° C., then cool to about 25° C. This may then be followed by heating and neutralizing for another 0.5 hours at a temperature of 50° C. to 150° C. This then would provide a preferred time and temperature of neutralization, prior to polymerization, of 1.0 hours at a temperature of 50° C. to 150° C.

With respect to the above disclosure regarding the control of neutralization of the acidic vinyl monomers, and in particular, the representative monomer of itaconic acid, it is noted that the use of partial neutralization, at the indicated neutralization temperatures and/or at the indicated neutralization times, may provide for the ability to minimize the isomerization of the vinyl acid monomer (e.g. itaconic acid) to chain terminating structures (i.e. compounds that impede the conversion itaconic acid to poly(itaconic acid). For example, the level of chain terminator, which may be formed from the acidic vinyl monomers may now be controlled to be present at or below the level of 20.0 mole percent, for each mole of acidic vinyl monomer that is initially present. More preferably, the level of chain terminator sourced from the acidic vinyl monomer may be controlled, through the neutralization procedures noted herein, to be present at levels of at or below 10.0 mole percent for each mole of acidic vinyl monomer, and in the most preferred embodiment, such level of chain terminator is controlled to be present at or below 5.0 mole percent. For example, the level of chain terminator may preferentially be adjusted to be in the range of 0.1 mole percent to 5.0 mole percent.

One representative example of the formation of chain terminator from a vinyl acidic monomer again points to the representative use of itaconic acid. More specifically, it is contemplated that itaconic acid may rearrange to provide citraconic acid or mesaconic acid, according to the following general equation, which citraconic or mesaconic acid, as a tri-substituted vinyl monomer, is believed to retard polymerization conversion and/or molecular weight.

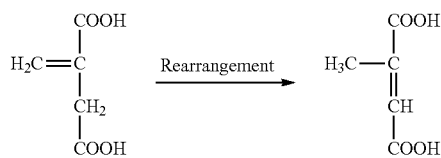

Polymerization

Subsequent to neutralization, according to the use of the partial neutralization noted herein at the indicated windows of, e.g., time and temperature, polymerization may be initiated. Initially, the vinyl monomers noted herein containing acidic functionality may be combined in a solvent to provide a solids content of 50 wt. % to 90 wt. %, including all values therein in 1.0 wt. % increments. The solids content may more preferably be in the range of 60 wt. % to 80 wt. % or 65 wt. % to 75 wt. %. Solids content may be understood as the wt. % of monomer in the solvent that is employed.

One may then employ radical initiation, utilizing free radical initiators such as peroxides and azo compounds, such as azobisisobutyronitrile (AIBN). One may also preferably utilize water-soluble radical initiators wherein the initiators are prepared in solution by dissolving the selected initiator in deionized water or a combination of water miscible polar solvents. Water soluble initiators may include persulfate salts, such as ammonium persulfate, sodium persulfate and potassium persulfate, including mixtures thereof. Also useful as a water soluble initiator are hydrogen peroxide ($H_2O_2$), tertiobutyl hydroperoxide, and water soluble azo initiators.

The initiators may be present at the concentration of 0.05 wt. % to 15.0 wt. % of monomer present, and all values therein, at 0.05 wt. % increments. More preferably, the initiators may be present at a level of 0.10 wt. % to 6.0 wt. % of monomer present, or at a level of 0.20 wt. % to 4.0 wt. % of the monomer present. In addition, the initiators may be selected such that they have an effective temperature for a 10.0 hour half-life $(T10)_{1/2}$, or time to decrease to half of their initial concentration, of less than or equal to 100° C.

In other words, preferentially, the initiators are selected such that less than half of the initiator remains present after 10 hours, at temperatures above 100° C. In this manner, it can be assured that sufficient free radicals are generated during the polymerization.

The initiator may be sequentially introduced into the polymerization solution (monomer and solvent) by introducing the herein disclosed amount of initiator over the first 75% of the time assigned for polymerization. For example, for a 3 hour polymerization period, one may introduce the initiator such that the first 50% of all initiator to be added is introduced at the start of the polymerization period, and the remaining 50% is added over the 2.25 hours. Furthermore, one may elect to add all of the desired amount of initiator at the start of the selected polymerization period. However, it may be preferred to utilize sequential addition, as this may support continuous polymerization processes.

The solution of monomer and solvent, subsequent to the neutralization procedures noted herein, may then be heated to a temperature of 50° C. to 150° C., including all values therein in 1.0° C. increments. More preferably, the polymerization temperature may be set to 70° C. to 115° C. or 80° C. to 110° C. In addition, the time for polymerization of the monomers may be from 0.1 hours to 48 hours, including all values therein, in 0.1 hour increments. More preferably, the time for polymerization may be set to a time period of 0.2 hours to 12.0 hours or 0.3 hours to 3.0 hours.

Polymer MW

The polymers produced herein preferably are formed with number average molecular weights (Mn) at 500-5000, including all values therebetween. Other more preferable ranges include 500 to less than 1000, 1000-5000, 2000-5000, 3000-5000 and 4000-5000. One particularly preferred range is 1500-3500.

Preferably, to achieve such Mn values of 500-5000 it has been found advantageous to now promote a chain transfer reaction during polymerization of the above referenced monomers. Specifically, an inorganic chain transfer agent, such as hypophorous acid is employed ($H_3PO_2$) which will react with sodium hydroxide to form sodium hypophosphite. The sodium hypophosphite then will react with the free-radical end of the growing polymer chain and serve as a chain transfer agent according to the general scheme noted below:

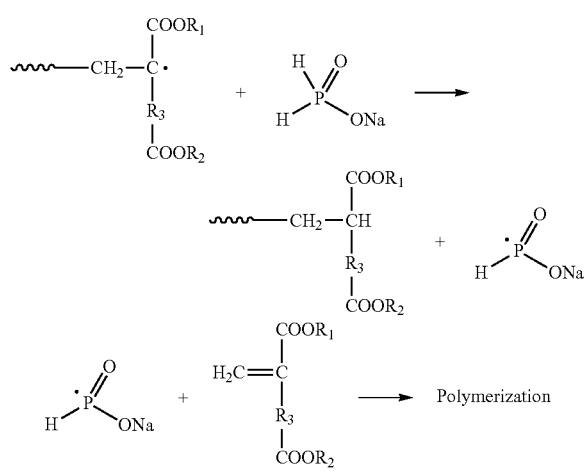

Accordingly, by use of the above indicated inorganic chain transfer agent (sodium hypophosphite) the Mn values, as noted, can be conveniently controlled to fall within the preferred range of 500-5000. This number average molecular weight window, in turn, facilitates the formation of the soluble compositions of the metal salt of polyitaconic acid as disclosed herein.

Polymer Tacticity

The polymers prepared herein, at the indicated Mn values of 500-5000 have a desired level of tacticity with respect to the analysis of triad structure by NMR techniques. For example, the polymers herein are formed with the presence of syndiotactic triads, at a level of greater than 58.0%. For example, the level of syndiotactic triads as determined by NMR techniques, such as $^{13}C$ NMR, may be formed at the level of greater than 58.0% to 75.0%, including all values therein, in 1.0% increments.

EXAMPLES

C-13 NMR Analysis: 13C NMRs were obtained with a Varian (500 MHz $^{1}H$) with 45° pulse angle, 12 s delay between pulses/re magnetization and 3000 accumulations. The experiments were performed at T=25° C. in 5 mm diameter NMR tubes. NMR samples had a concentration of approximately 0.25 g/g in $D_2O$. A drop of 1,4-dioxane was added to each sample as reference (peak at 67.4 ppm). The pH was adjusted with a solution of hydrochloric acid at 12N. All samples had pH between 0.2 and 1.5. Tacticity was determined from the chemical shifts of the triads from the beta carbonyl with the following assignments:

178.7 ppm rr triad (s-syndiotactic)
178.2 ppm mr triad (h-atactic or heterotactic)
177.6 ppm mm triad (i-isotactic)

Syndiotacticity is calculated as the ratio of the area of the rr triad over the area of all triads (rr+mr+mm).

"Synthesis A" was conducted using the representative monomer itaconic acid; 2,2'-azodiisobytyronitrile(AIBN), hydrogen peroxide; tert-butyl hydroperoxide (tBHP); ferric ammonium sulfate; toluene; Span 80; and hydrochloric acid, without further purification. 50 g (0.385 mol) of itaconic acid was half neutralized with 5 g (0.385 mol) sodium hydroxide, and was dissolved in 25 ml deionized water into a flask, and 8 mg ferric ammonium sulfate was added. The mixture was heated to 80° C. and 25 ml tBHP (70 wt % in water); 50 ml H202 (35 wt % in water) were fed by syringe pump for 2 hours, and heat was maintained for an additional 4 hours. The product was dried at 25° C. under vacuum for 10 hours.

Figure 2:
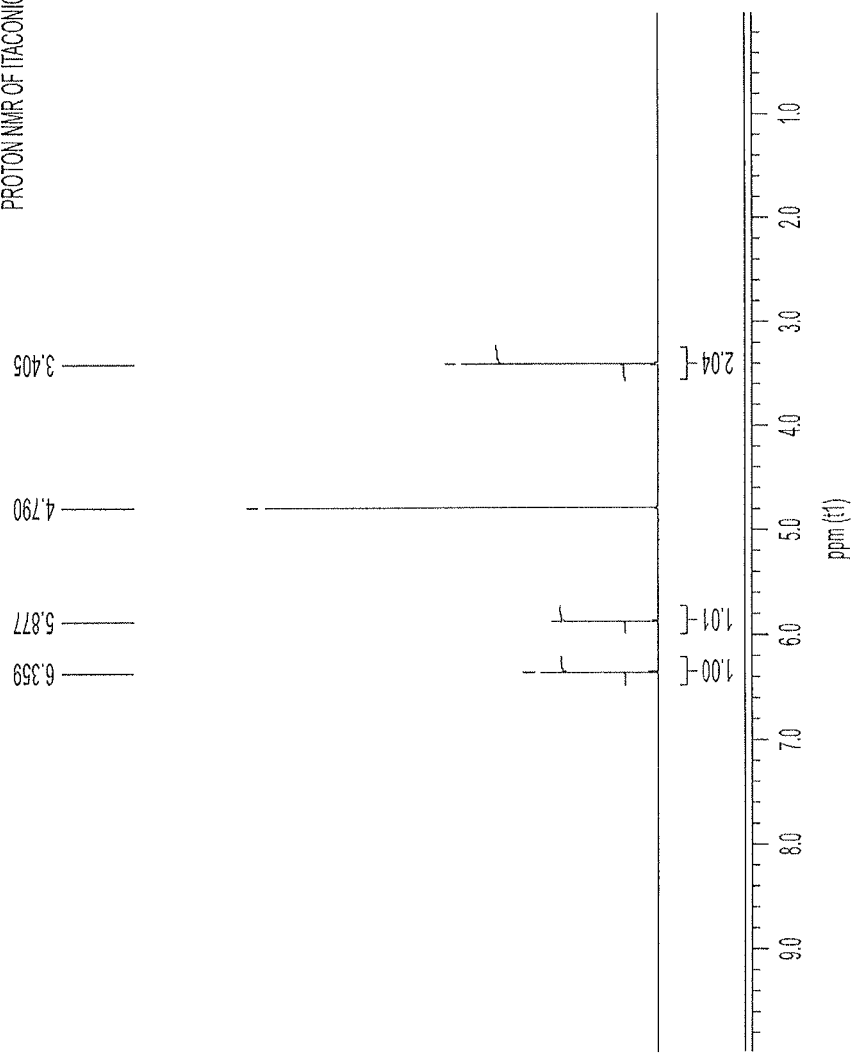
FIG. 2 shows the 400 MHz $^1$H NMR spectra of itaconic acid monomer in $D_2O$.

A Varian 400 MHz NMR was used to investigate the structure of the resulting polymers. FIG. 1 shows the $^{1}H$ NMR spectra for Synthesis A, where the two vinylic proton peaks in the itaconic acid monomer, as shown in FIG. 2, disappeared completely, and the IR spectra for Synthesis A supports it, and two distinct peaks with the similar area around 2.7 ppm and 2.0 ppm describe the $CH_2$ in the side group and backbone separately, indicating the structure of poly(itaconic acid). The sample from Synthesis A analyzed by $^{1}H$ NMR was not precipitated in acetone, and the calculated polymerization yield was 100%. However, some additional sharp peaks were observed in the $^{1}H$ NMR indicating an extensive and complex reaction of the large quantity of the redox initiator.

Figure 3:
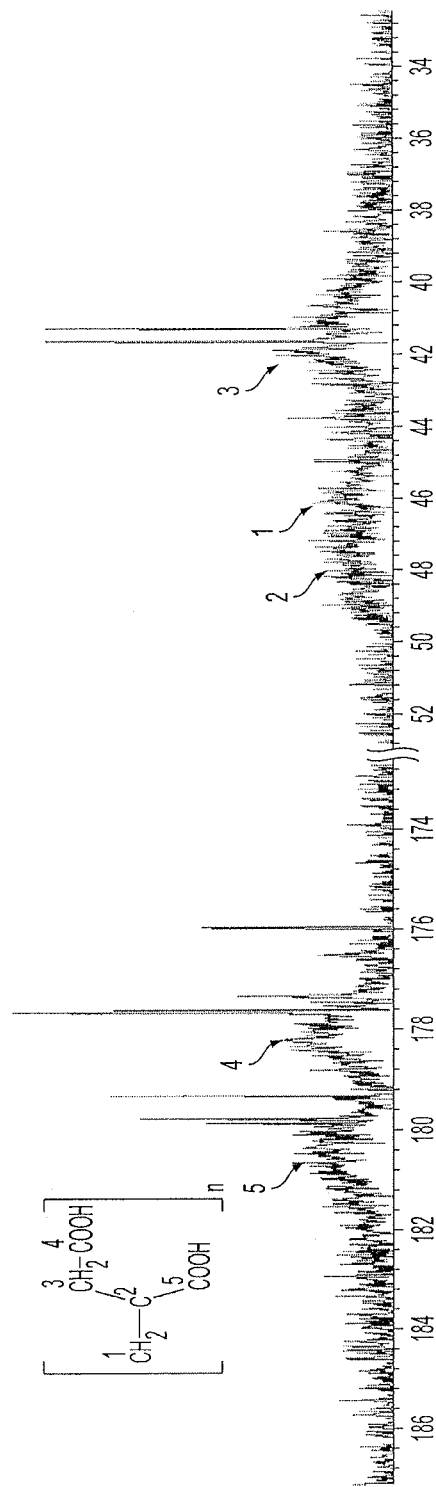
FIG. 3 shows the 400 MHz $^{13}$C NMR spectra of poly (itaconic acid) in $D_2O$ corresponding to Synthesis A.
Figure 4:
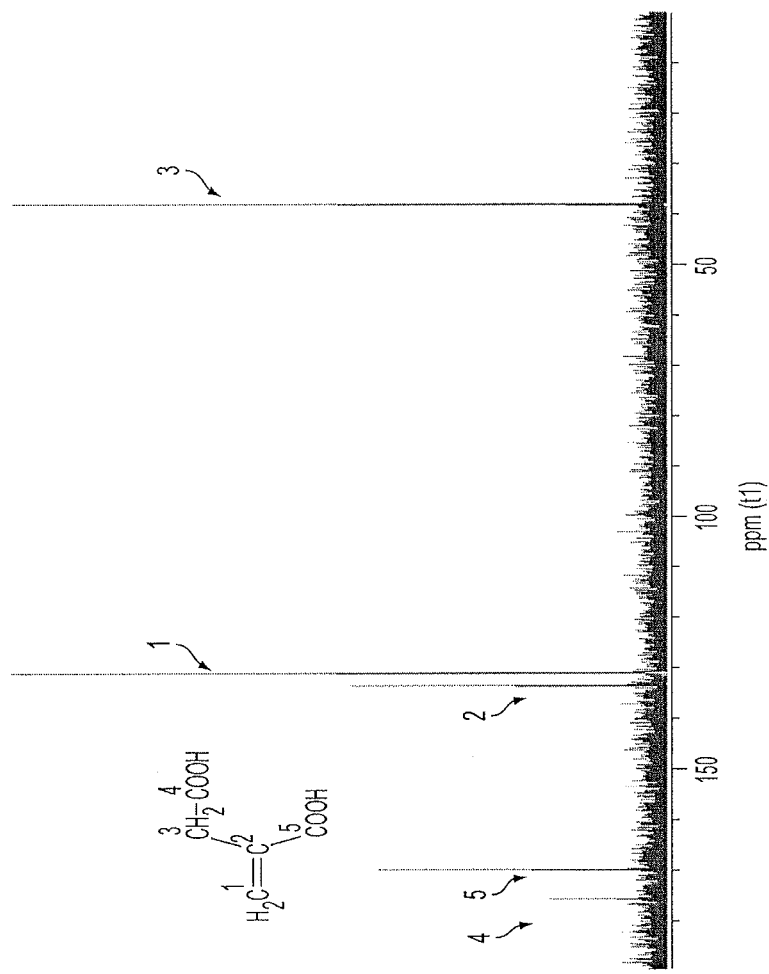
FIG. 4 shows the 400 MHz $^{13}$C NMR spectra of itaconic acid.

The five resonance frequencies of the $^{13}C$ NMR spectra of the Synthesis A and itaconic acid monomer, as shown in FIGS. 3 and 4, are compared in Table 1.

TABLE 1

| Carbon | C1 | C2 | C3 | C4 | C5 |
|---|---|---|---|---|---|
| Chemical Shifts For Itaconic Acid (ppm) | 128.0 | 130.5 | 36.8 | 176.2 | 171.1 |
| Chemical Shifts For Poly(itaconic acid) (ppm) | 47.8 | 49.2 | 42.8 | 178.9 | 180.6 |

After polymerization, the chemical shifts of the carbons in side groups do not change much. However, the carbons C1 and C2 of the double bond in the monomer are absent and its resonance is shifted to 45.8 and 47.2 ppm, which is a sign for the formation of a polymer backbone.

Example I 100 grams of itaconic acid and 50 grams of deionized water were added to a 250 ml plastic beaker and 30.8 grams of sodium hydroxide was added slowly with manually stifling while the beaker was kept cold with an ice water bath. The solution was then added to a 250 milliliter, 3-neck round bottom flask equipped with a mechanical stirrer, nitrogen feed line, water cooled condenser, and thermometer. After the flask content was heated to 100 degree centigrade, 1 ml of 70% tertiobutyl hydroperoxide aqueous solution was added. The reaction was then held for two and a half hours, then cooled down.

Figure 5:
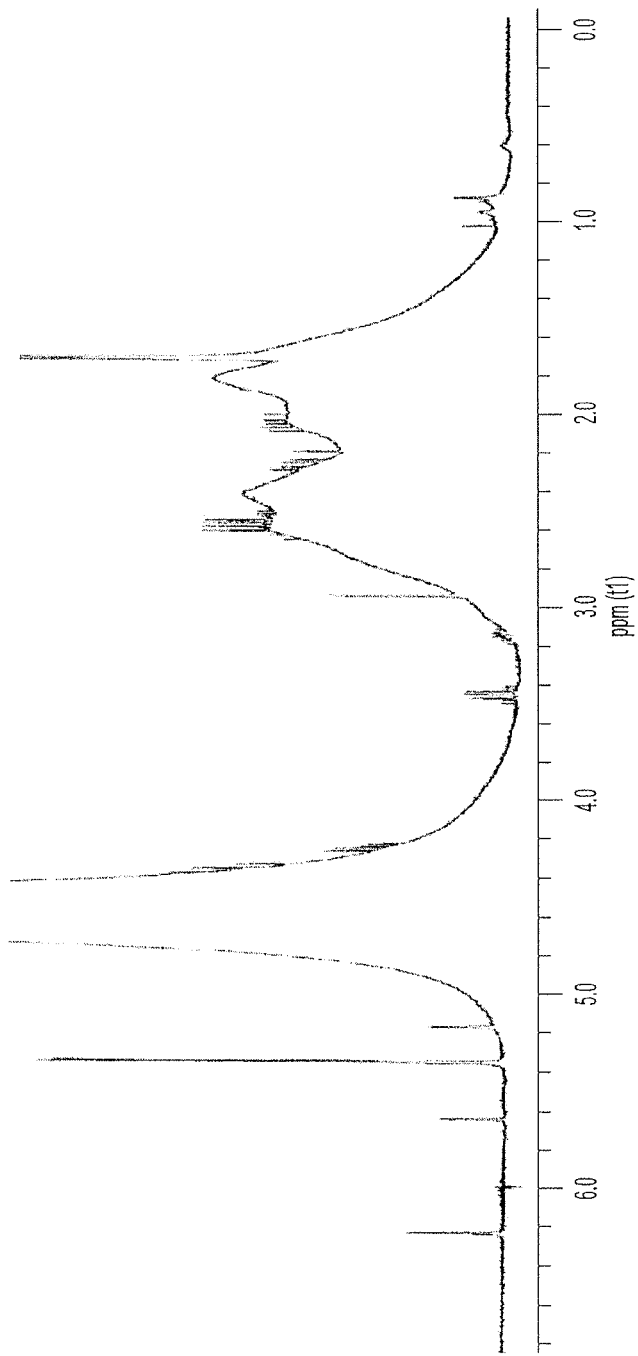
FIG. 5 shows the 400 MHz $^1$H NMR spectra of poly(itaconic acid) in $D_2O$ corresponding to Example I.
Figures 6A, 6B:
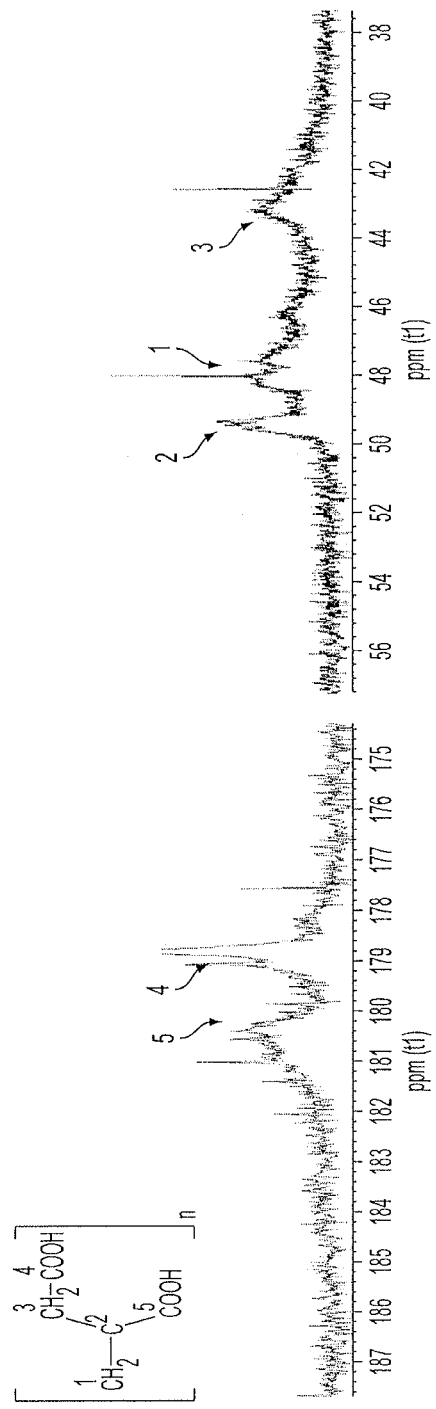
FIG. 6a shows the 400 MHz $^{13}$C NMR spectra of poly (itaconic acid) at the chemical shift/ppm of 187 to 175 corresponding to Example I.
FIG. 6b shows the 400 MHz $^{13}$C NMR spectra of poly (itaconic acid) at the chemical shift/ppm of 56 to 38 corresponding to Example I.

The resultant solution showed 97.7 percent conversion of the itaconic acid into a polymer by NMR. FIG. 5 shows the $^{1}H$ NMR of this same in D20 used for the quantification of the polymerization yield. Based on gel permeation chromatography, the average molecular weight was 10,180 g/mole, and the number average molecular weight (Mn) was 3,920 g/mole, in polyacrylic acid equivalent molecular weight. FIGS. 6a and 6b show the $^{13}C$ NMR of this sample with the same peak assignment as used in Table 1, providing evidence for the synthesis of polyitaconic acid.

Example II

The procedure of EXAMPLE I was repeated except 2 milliliter of 70% tertbutyl hydroperoxide was added after reaching 100 degree centigrade. The reaction was then held for 155 minutes and then cooled down. The resultant solution showed 90.3 percent conversion of the itaconic acid into a polymer by NMR. Based on gel permeation chromatography, the weight average molecular (Mw) was 7,690, and the number average molecular weight (Mn) was 3,390 g/mole in polyacrylic acid equivalent molecular weight.

Example III 4000 gr of itaconic acid was placed in a 10 L kneader-reactor at 70 C. 2462 grams of sodium hydroxide at 50 wt % in water was added over 12 minutes. 170 grams of 70% tertiobutyl hydroperoxide was added at once. The reactor was pressurized to 0.5 bar above atmospheric pressure with nitrogen then heated to 100° C. Mixing and heating were maintained for 65 minutes, and then the reactor was cooled down. The resultant material showed 99 percent conversion of the itaconic acid into a polymer as analyzed by $^1$H-NMR. $^{13}$C-NMR analysis of the triads in the 177-178 ppm region resulted in a 64% syndiotacticity at pH=0.82. Based on gel permeation chromatography, the weight average molecular (Mw) was 18,586 g/mole, and the number average molecular weight (Mn) was 4,364 g/mole in polyacrylic acid equivalent molecular weight.

Example IV 650 gr of itaconic acid and 400 grams of sodium hydroxide at 50 wt % solution in water were co-added over 15 minutes into a 1L jacketed reactor at 70° C. under mechanical stirring under nitrogen atmosphere. The reactor was then heated to 100° C. and 80 ml of 70 wt. % tertiobutyl hydroperoxide in water was added at once. Mixing and heating were maintained for 120 minutes, and then the reactor was cooled down. The resultant material showed 98.7 percent conversion of the itaconic acid into a polymer as analyzed by $^1$H-NMR. $^{13}$C-NMR analysis of the triads in the 177-178 ppm region resulted in a 62% syndiotacticity. Based on gel permeation chromatography, the weight average molecular (Mw) was 12,800 g/mole, and the number average molecular weight (Mn) was 4,574 g/mole in polyacrylic acid equivalent molecular weight.

Example V 650 gr of itaconic acid and 400 grams of sodium hydroxide at 50 wt % solution in water were co-added over 15 minutes into a 1L jacketed reactor at 70 C under mechanical stifling under nitrogen atmosphere. The reactor was then heated to 90° C. and 60 ml of 50 wt % hydrogen peroxide in water was added at once. Mixing and heating were maintained for 60 minutes, and then the reactor was cooled down. The resultant material showed 94 percent conversion of the itaconic acid into a polymer as analyzed by $^1$H-NMR. Based on gel permeation chromatography, the weight average molecular (Mw) was 10,975 g/mole, and the number average molecular weight (Mn) was 3,795 g/mole in polyacrylic acid equivalent molecular weight.

Example VI 67.7 gr of itaconic acid, 23.0 grams of sodium hydroxide at 50 wt % solution in water and 9.3 grams of pure sodium hydroxide were co-added over 15 minutes into a 250 ml round bottom flask at 80 C with magnetic stirring under nitrogen atmosphere. The reactor was then heated to 100° C. and 3.1 ml of 70 wt. % tertiobutyl hydroperoxide in water was added at once. Mixing and heating were maintained for 60 minutes, and then the reactor was cooled down. The resultant material showed 98.1 percent conversion of the itaconic acid into a polymer as analyzed by $^1$H-NMR. $^{13}$C-NMR analysis of the triads in the 177-178 ppm region resulted in a 62% syndiotacticity at pH=0.20. Based on gel permeation chromatography, the weight average molecular (Mw) was 9,159 g/mole, and the number average molecular weight (Mn) was 3,573 g/mole in polyacrylic acid equivalent molecular weight.

Commercial Poly(itaconic acid)

A poly(itaconic acid) was made available from 'Monomer-Polymer and Dajac Labs, Inc." and analyzed. The commercial polymer showed 48% percent of purity in polymer as analyzed by $^1$H-NMR. Purification/concentration was required in order to perform the $^{13}$C-NMR analysis. and was done with a 3000MWCO filter by centrifugation. $^{13}$C-NMR analysis of the triads in the 177-178 ppm region resulted in a 52% syndiotacticity (pH=0.94). Based on gel permeation chromatography, the weight average molecular (Mw) was 19600 g/mole, and the number average molecular weight (Mn) was 3700 g/mole in polyacrylic acid equivalent molecular weight.

Comparative Polymerization I

To a one neck glass round bottom flask equipped with a reflux condenser and a magnetic stirrer, was added 50 ml 0.5M HCl, 10 g of itaconic acid and 0.60 g of potassium persulfate. The content was heated at 60° C. during 68 hours. The polymer solution was precipitated in acetone (HPLC grade). Filtration was performed and the solid obtained was dried in the oven at 50° C. $^{13}$C-NMR analysis of the triads in the 177-178 ppm region resulted in a 46.5% syndiotacticity (pH=1.05). Based on gel permeation chromatography, the weight average molecular weight (Mw) was 17,800 g/mole, and the number average molecular weight (Mn) was 8,800 g/mole in polyacrylic acid equivalent molecular weight. It is noted that this comparative polymerization I is based upon method A reported in: "Polymerization of Itaconic Acid In Aqueous Solution: Structure Of The Polymer And Polymerization Kinetics At 25° C. Studied By Carbon-13 NMR", Grespos et al, Makromolekulare Chemie, Rapid Communications (1984), 5(9), 489-494.

Comparative Polymerization II

To a three neck glass round bottom flask equipped with a reflux condenser, a magnetic stirrer, under nitrogen atmosphere, was added 83 ml of m-xylene, 7.5 g of itaconic anhydride and 0.17 g of AIBN. The reaction mixture was heated at 60° C. for 2 days. The resulting poly(itaconic anhydride) was filtered, washed with m-xylene and ethyl ether. The solid (4.6 g) was then mixed with 15 ml of water overnight. The solution was dried under vacuum (10 mmHg) at 50° C. The resultant material showed 83 percent pure in polymer as analyzed by $^1$H-NMR. $^{13}$C-NMR analysis of the triads in the 177-178 ppm region resulted in a 34% syndiotacticity (pH=0.88). Based on gel permeation chromatography, the weight average molecular weight (Mw) was 7,505 g/mole, and the number average molecular weight (Mn) was 2,915 g/mole in polyacrylic acid equivalent molecular weight. It is noted that this comparative polymerization II is based upon method C reported in: "Polymerization of Itaconic Acid In Aqueous Solution: Structure Of The Polymer And Polymerization Kinetics At 25° C. Studied By Carbon-13 NMR", Grespos et al, Makromolekulare Chemie, Rapid Communications (1984), 5(9), 489-494.

Comparative Polymerization III

To a three neck glass round bottom flask equipped with a reflux condenser, a magnetic stirrer, under nitrogen atmosphere, was added 11.6 ml of deionnized water. The flask was heated at 90° C. A monomer solution of 20.45 g of itaconic acid, 12.35 g of 50 percent NaOH and 7 g of DI water was prepared. An initiator solution of 1.75 g of potassium persulfate and 25.8 g of water was also prepared. The monomer and initiator solutions were fed into the flask linearly and separately over 2 hours, while maintaining the flask at a temperature sufficient to continue to reflux the mixture, about 100° C. When the addition was complete, the polymer solution was held at temperature for an additional 30 min. The resultant polymer solution had a conversion of 35% (estimated by GPC). The solution was precipitated in acetone. The solid was dried at 50° C. Further purification had to be done to provide quality NMR data. 1 g of product was dissolved in 2 g of $D_2O$ and introduced in a 3000MW filter centrifuge tube. After centrifugation at 8000 rpm for 10 minutes, the retentate was washed twice with 1 ml of D20 and the pH was adjusted to 0.53. $^{13}$C-NMR analysis of the triads in the 177-178 ppm region resulted in a 49% syndiotacticity. Based on gel permeation chromatography, the weight average molecular weight (Mw) was 1,400 g/mole, and the number average molecular weight (Mn) was 1,000 g/mole in polyacrylic acid equivalent molecular weight. It is noted that this comparative polymerization III is based upon Example I in U.S. Pat. No. 5,336,744.

Comparative Polymerization IV

To a three neck glass round bottom flask equipped with a reflux condenser, a magnetic stirring, under nitrogen atmosphere, was added 23.95 ml of deionnized water, 20.45 g of itaconic acid and 12.35 g of 50 wt % percent NaOH. An initiator solution of 1.54 g of sodium persulfate and 5.79 ml of deionized water was also prepared. The initiator solution was fed into the flask over 2 hours, while maintaining the flask at a temperature sufficient to continue to reflux the mixture, about 100° C. When the addition was complete, the polymer solution was held at temperature during 30 min. The resultant polymer solution had a conversion of 36% (estimated by GPC). The resultant polymer solution was precipitated in acetone. The solid was dried at 50 C. The resulting material was further purified. 1 g of product was dissolve in 2 g of $D_2O$ and introduce in a 3000MW filter centrifuge tube. After centrifugation at 8000 rpm for 10 minutes, the retentate was washed twice with 1 ml of $D_2O$ and the pH was adjusted to 0.75. $^{13}$C-NMR analysis of the triads in the 177-178 ppm region resulted in a 53% syndiotacticity. It is noted that this comparative polymerization IV is based upon Example II in U.S. Pat. No. 5,336,744.

Soluble Aqueous Solutions of Metal Salts of Polyitaconic Acid

The preparation of a soluble solution of a metal salt of polyitaconic acid herein of Mn values of 500-5000 is carried out such that preferably, apart from controlling Mn values between 500-5000 and syndiotacticity of at least 58%, one combines a metal such as Zn with the polyitaconic acid wherein the weight ratio of Zn to polyitaconic acid (Zn/PIA) is in the range of 0.01-0.15, and all values therein, at 0.01 increments. Accordingly, the Zn/PIA ratio may have a value of 0.01, 0.02, 0.03, 0.04, 0.05, 0.06, 0.07, 0.08, 0.09, 0.10, 0.11, 0.12, 0.13, 0.14 or 0.15, as well as any range between these values. For example, the Zn/PIA ratio may preferably have a value in the range of 0.01-0.09, or 0.05-0.15, or 0.10-0.15.

The concentration of PIA in the aqueous solution is preferably 5-15% by weight, including all values and increments therein. Accordingly, the PIA may be present in the aquous solution at a level of 5%, 6%, 7%, 8%, 9%, 10%, 11%, 12%, 13%, 14% and 15% by weight. One particular preferable range is 6-12% by weight.

The concentration of Zn in the aqueous solution 0.5-2.0% by weight, including all values and increments therein. Accordingly, the Zn may be present at 0.5, 0.6, 0.7, 0.8, 0.9, 1.0, 1.1, 1.2, 1.3, 1.4, 1.5, 1.6, 1.7, 1.8, 1.9 and 2.0% by weight. One particularly preferable range is 0.8-1.5% by weight.

In addition, the pH of the soluble solution is also preferably controlled. More specifically, the pH is preferably in the range of 3.0-11.0. Accordingly, the pH may be 3.0, 4.0, 5.0, 6.0, 7.0, 8.0, 9.0, 10.0, and 11.0. The control of pH may be achieved by treatment of, e.g, the soluble solution of the metal salt of polyitaconic acid with 1N HCl in order to reduce the pH values. By contrast, higher pH values may be achieved by treatment of the soluble solution of the metal salt of polyitaconic acid with 15% KOH solution. It can be noted that at pH values of less than 7.0, the soluble solutions may be particularly useful as cleaning solutions, such as cleaning solutions for toilets, showers, bathrooms, etc. At pH value of greater than pH 7.0, the soluble solutions are particularly useful as laundry detergents and fabric cleaning. At pH levels of 6.2-7.8 the soluble solutions may be used as mouthwash and hard surface cleaners (countertops).

Without being bound by any particular theory, it is believed that it is now possible to obtain a fully soluble aqueous composition that includes the above indicated relative amount of Zn, which solubility and Zn levels provide improved performance to the consumer for the identified applications. Specifically, the selection of Mn values of 500-5000 is believed to provide a greater relative number of polymer chains that may enter into solution and lower relative viscosity and still offer sufficient interaction with Zn. Moreover, the feature of being primarily in a syndiotactic conformation allows the PIA maximum repulsion (greatest relative distance) between ionic groups along the polymeric backbone, which in turn allows for a higher relative degree of rotational freedom and a more favorable energy state which in turn provides for improved solubility of the PIA and interaction with Zn at Mn values of 500-5000 (as noted above, a concentration of PIA in the aqueous composition of 5-15% by weight and the concentration of Zn in the aqueous solution of 0.5-2.0% by weight).

It should also be noted that the above described soluble aqueous solution of the Zn salt of PIA, which is preferably supplied as a stock solution, may be further diluted depending upon a particular commercial application at issue. In such regard, dilution of the above described soluble aqueous solutions may be such that a selected amount of water is added to reduce the concentration of PIA and Zn by a factor up to 10. That is, the concentration of PIA in such diluted solution, if initially at 5% by weight may be lowered to 0.5% by weight. If the initial concentration of Zn is 0.5%, the corresponding concentration of Zn may be lowered to 0.05% by weight. Accordingly, diluted solutions of the above described soluble aqueous solutions may be diluted from an initial PIA concentration of 5-15% by weight to provide a concentration of PIA of 0.5% or greater, or preferably in the range of 0.5-1.5% by weight. The initial concentration of Zn at 0.5-2.0% by weight may be diluted to provide a concentration of Zn of 0.05% or greater, or preferably in the range of 0.05-0.2% by weight.

Example 1

PIA/Zn Salt Preparation; Post Polymerization 10.24 g of politaconic acid having a Mn of about 2000 was partially neutralized with sodium (83% active) and was dissolved in 88.21 g of RO water. A clear lightly yellow solution was formed. 1.55 g of zinc oxide was added to this solution forming a milky mixture. After 6 hours of stirring with a magnetic stir bar a clear yellow solution with pH 7 was formed.

Example 2

In-Situ PIA/Zn Salt Preparation—During Polymerization 77.59 g of zinc oxide was combined with water, creating a thick paste. This paste was introduced into the 816.76 g itaconic acid and 22.4 g of sodium hypophosphite mixture, and added to a 5 L reactor. 346.24 g of 50% solution of sodium hydroxide was added and the whole mixture was stirred for five minutes. After this time 54.18 g of 33% sodium persulfate was added and stirred for another 5 minutes. The content of the reactor was drained. The product was left to dry overnight before grinding and testing. Molecular weight and conversion (as tested by GPC) was as follow: Mn=2054.7 g/mol, Mw=5568.3 g/mol, Conversion=>94%

Example 3

Stable Odor Absorbing Formulation with PIA/Zn

A formulation containing zinc/sodium politaconate was prepared as follow: 0.04 g of perfume (DAWN CLASSIC Blue Type Y 14713 from Continental Aromatics) was stirred with 1.6 g of Polysorbate 20 until uniform mixture formed. Then 0.04 g of the preservative (phenoxyethanol) was added. A clear solution formed when 13.62 g of water was added to this mixture. 4.7 g of PIA/Zn salt (solution described in Example 1 filtered through 0.4 micron filter) was added forming slightly yellow solution. The solution was stable at room temperature.

Example 4

Stability of Example 3 Formulation at Different pH

The pH of the formulation described in Example 3 was adjusted to pH 3 with 0.2 g of 1N hydrochloric acid. This solution was stable (no precipitation was formed). The pH of the formulation described in Example 3 was adjusted to pH 10 with 15% potassium hydroxide. This solution was stable (no precipitation was formed).

Example 5

Stability of DSP/Zn Salt in Hard Water 11.75 g of solution described in Example 1 (filtered through 0.2 micron filter) was diluted with 38.25 g hard water (300 ppm total hardness water). The solution formed had a slightly yellow color and was stable (no precipitation was formed).

It should also be appreciated that all of the various embodiments noted herein are interchangeable and features within any of the drawings may be used within each of the respective drawings, to optimize any and all of the disclosed characteristics of the polymerizations noted herein and the utility of the polymers cleaning and odor control applications.

The foregoing description of several methods and embodiments has been presented for purposes of illustration. It is not intended to be exhaustive and obviously many modifications and variations are possible in light of the above teaching.

What is claimed is:

1. A soluble aqueous composition of a zinc salt of a polyacid comprising the following repeating units:

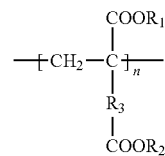

wherein $R_1$ and $R_2$ are selected from a hydrogen atom or an alkyl group or an aromatic group, or a cyclic alkyl group or a polyether, and combinations thereof and $R_3$ may be selected from an alkyl group, aromatic functionality, hetero aromatic functionality, cyclic alkyl group, heterocylic group, or combinations thereof, wherein at least 50 mole % of $R_1$ and $R_2$ are a hydrogen atom to provide carboxylic acid functionality for zinc salt formation;
wherein the weight ratio of Zn to the polyacid is in the range of 0.01-0.15 and the concentration of the polyacid in the aqueous composition is 5-15% by weight and the concentration of Zn in the aqueous solution is 0.5-2.0% by weight and the pH of said aqueous composition is in the range of 3.0-11.0.

2. The composition of claim 1 wherein said polyacid has $^{13}$C NMR triads having a syndiotacticity of greater than 58.0%.

3. The composition of claim 1 wherein the value of n for the indicated repeating unit provides a number average molecular weight (Mn) of 500-5000.

4. The composition of claim 1 wherein $R_1$ and $R_2$ are selected from a hydrogen atom and $R_3$ comprises a methylene linkage.

5. The composition of claim 1 wherein said polyacid indicates $^{13}$C NMR triad having a syndiotacticity of 58% to 75%.

6. The composition of claim 1 wherein said Mn value is in the range of 1500-3500.

7. The composition of claim 1 wherein the weight ratio of Zn to said polyacid is in the range of 0.01-0.09.

8. The composition of claim 1 wherein the concentration of the polyacid in the aqueous solution is 6-12% by weight.

9. The composition of claim 1 wherein the concentration of Zn in the aqueous solution is 0.8-1.5% by weight.

10. The composition of claim 1 wherein the pH is less than 7.0.

11. The composition of claim 1 wherein the pH is greater than 7.0.

12. The composition of claim 1 wherein the pH is in the range of 6.2-7.8.

13. The composition of claim 1 wherein the soluble aqueous solution containing the polyacid at 5-15% by weight and Zn at 0.5-2.0% by weight is diluted with additional water and provides an aqueous solution with the polyacid present at 0.5-1.5% by weight and the Zn present at 0.05-0.2% by weight.

14. The composition of claim 1 wherein said zinc salt of said polyacid comprises a portion of a copolymer of a vinyl type monomer.

15. The composition of claim 14 wherein said vinyl type monomer comprises acrylate monomer, vinyl acetate, vinyl halides, styrene, acrylamides, olefin monomers or acrylonitrile.

16. The composition of claim 1 wherein said zinc salt of said polyacid comprises a portion of a copolymer of a vinyl type anhydride monomer.

17. The composition of claim 16 wherein said zinc salt of said polyacid comprises maleic acid anhydride or itaconic acid anhydride.

* * * * *

UNITED STATES PATENT AND TRADEMARK OFFICE
CERTIFICATE OF CORRECTION

PATENT NO. : 9,284,446 B2  
APPLICATION NO. : 14/582637  
DATED : March 15, 2016  
INVENTOR(S) : Martin Vince et al.

Page 1 of 1

It is certified that error appears in the above-identified patent and that said Letters Patent is hereby corrected as shown below:

In the claims,

In column 14, line 17-18, in claim 1, delete "heterocylic," and insert -- heterocyclic, --, therefor.

Signed and Sealed this
Twenty-eighth Day of June, 2016

Michelle K. Lee
*Director of the United States Patent and Trademark Office*